(12) United States Patent
Wang et al.

(10) Patent No.: US 11,039,776 B2
(45) Date of Patent: Jun. 22, 2021

(54) DETERMINING BIPOLAR ELECTRICAL ACTIVITY

(71) Applicant: CARDIOINSIGHT TECHNOLOGIES, INC., Independence, OH (US)

(72) Inventors: Yong Wang, St. Louis, MO (US); Qing Lou, Powell, OH (US); Qingguo Zeng, Solon, OH (US); Ping Jia, Solon, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 497 days.

(21) Appl. No.: 15/934,619

(22) Filed: Mar. 23, 2018

(65) Prior Publication Data

US 2019/0290154 A1 Sep. 26, 2019

(51) Int. Cl.
*A61B 5/316* (2021.01)
*A61N 1/32* (2006.01)
*A61B 5/349* (2021.01)

(52) U.S. Cl.
CPC ............. *A61B 5/316* (2021.01); *A61B 5/349* (2021.01); *A61N 1/32* (2013.01)

(58) Field of Classification Search
CPC .......................... A61B 5/04012; A61B 5/0452
(Continued)

(56) References Cited

U.S. PATENT DOCUMENTS

| 5,146,926 A | 9/1992 | Cohen |
| 5,483,968 A | 1/1996 | Adam et al. |

(Continued)

FOREIGN PATENT DOCUMENTS

| EP | 2745773 A3 | 7/2014 |
| WO | 2003/028801 A2 | 4/2003 |

(Continued)

OTHER PUBLICATIONS

H.S. Oster, B. Taccardi, R.L. Lux, P.R. Ershier, Y. Rudy, "Noninvasive Electrocardiographic Imaging: Reconstruction of Epicardial Potentials, Electrograms and Isochrones, and Localization of Single and Multiple Electrocardiac Events", Circulation 1997; 96: 1012-1024.

(Continued)

*Primary Examiner* — Nadia A Mahmood
(74) *Attorney, Agent, or Firm* — Tarolli, Sundheim, Covell & Tummino LLP

(57) ABSTRACT

This disclosure provides one or more computer-readable media having computer-executable instructions for performing a method. The method includes storing geometry data representing a primary geometry of a cardiac envelope that includes nodes distributed across the cardiac envelope and geometry of a body surface that includes locations where electrical signals are measured. The body surface is spaced apart from the cardiac envelope. The method also includes perturbing the primary geometry of the cardiac envelope a given distance and direction to define the perturbed geometry of the cardiac envelope including nodes spaced from the nodes of the primary geometry. The method also includes computing reconstructed bipolar electrical signals on the nodes of the primary cardiac envelope based on the electrical signals measured from the body surface and the geometry data, including the primary and perturbed geometries of the cardiac envelope.

26 Claims, 7 Drawing Sheets

(58) Field of Classification Search
USPC .......................................................... 607/74
See application file for complete search history.

(56) References Cited

U.S. PATENT DOCUMENTS

| | | | |
|---|---|---|---|
| 6,047,206 | A | 4/2000 | Albrecht et al. |
| 6,718,291 | B1 | 4/2004 | Shapiro et al. |
| 6,772,004 | B2 | 8/2004 | Rudy |
| 6,856,830 | B2 | 2/2005 | He |
| 6,975,900 | B2 | 12/2005 | Rudy et al. |
| 7,016,719 | B2 | 3/2006 | Rudy et al. |
| 8,682,626 | B2 | 3/2014 | Ionasec et al. |
| 2002/0128565 | A1 | 9/2002 | Rudy |
| 2003/0120163 | A1 | 6/2003 | Rudy et al. |
| 2008/0058657 | A1 | 3/2008 | Schwartz et al. |
| 2008/0114257 | A1 | 5/2008 | Molin et al. |
| 2009/0053102 | A2 | 2/2009 | Rudy et al. |
| 2009/0275827 | A1 | 11/2009 | Aiken et al. |
| 2010/0191131 | A1 | 7/2010 | Revishvili et al. |
| 2011/0172545 | A1 | 7/2011 | Grudic et al. |
| 2013/0197884 | A1 | 8/2013 | Mansi et al. |
| 2014/0235986 | A1 | 8/2014 | Harlev et al. |
| 2015/0133759 | A1 | 5/2015 | Govari |
| 2015/0164357 | A1* | 6/2015 | Zeng .................. A61B 5/7278 600/509 |
| 2016/0143541 | A1 | 5/2016 | He et al. |
| 2017/0332971 | A1 | 11/2017 | MacNeil et al. |

FOREIGN PATENT DOCUMENTS

| | | |
|---|---|---|
| WO | 2005/072607 A1 | 8/2005 |
| WO | 2008/085179 A1 | 7/2008 |
| WO | 2012/109618 A2 | 8/2012 |
| WO | 2014/118535 A3 | 8/2014 |

OTHER PUBLICATIONS

J.E. Burnes, B. Taccardi, Y. Rudy, "A Noninvasive Imaging Modality for Cardiac Arrhythmias" Circulation Oct. 24, 2000; 102: 2152-2158.

C. Ramanathan, R.N. Ghanem, P. Jia, K. Ryu, Y. Rudy, "Electrocardiographic Imaging (ECG): A Noninvasive Imaging Modality for Cardiac Electrophysiology and Arrhythmia" Nature Medicine, Mar. 2004; 10:422-428.

A. Eisenberg, Beyond the EKG, to a Hypersensitive heart monitor. New York Times. Apr. 22, 2004.

M.A. Goldberg and C.S. Chen, The Method of Fundamental Solutions for potential, Helmholtz and diffusion problems, in Boundary Integral Methods—Numerical and Mathematical Aspects, ed. M.A. Goldberg, Computational Mechanics Publications, 1998, DD. 103-176.

M.A. Goldberg, C.S. Chen & A.S. Muleshkov, The Method of Fundamental solutions for diffusion equations, Boundary Element Technology XIII, eds. C.S. Chen, C.A. Brebbia, D.W. Pepper, WIT Press, Boston, Southampton, pp. 377-386, 1999.

Y.C. Hon, T. Wei, A fundamental solution method for inverse heat conduction problems. Engineering Analysis with Boundary Elements, vol. 28, Issue 5, pp. 489-495, May 2004.

Y.C. Hon and T. Wei, The method of fundamental solution for solving multidimensional inverse heat conduction problems, CMES-Comp. Model. Eng. 7, 119-132 (2005).

Divo et al.; "A Mesh less Method for Conjugate Heat Transfer Problems"; Engineering Analysis with Boundary Elements 29 (2005) 136-149.

Fischer, G. et al., "Application of high-order boundary elements to the electrocardiographic inverse problem", Computer Methods and Programs in Biomedicine Elsevier Ireland, vol. 58, No. 2, (1999) pp. 119-131.

Karageorghis, Andreas and Fairweather, Graeme, "The Method of Fundamental Solutions for the Numerical Solution of the Biharmonic Equation", Journal of Computation Physics, London, GB, vol. 69, No. 2, Apr. 1, 1987 (Apr. 1, 1987), pp. 434-459.

Seger, M. et al., Lead Field Computation for the Eletrocardiographic inverse problem—finite elements versus boundary elements•: Computer Methods and Programs in Biomedicine Elsevier Amsterdam, NL, vol. 77, No. 3, Mar. 1, 2005 (Mar. 1, 2005), pp. 241-252.

Rudy Y., et al: "The Inverse Problem in Electrocardiography: Solutions in Terms of Epicardial Potentials", Critical Reviews in Biomedical Engineer, CRC Press, Boa Raton, FL, US, vol. 16, No. 3, Jan. 1, 1988, pp. 215-268.

Jeongjin Roh, High-Performance Error Amplifier for Fast Transient DC-DC Converters, Express Briefs, vol. 52, No. 9, Sep. 2005.

Ye [Scedil] Im Serinagaoglu et al: "Multielectrode Venous Catheter Mapping as a High Quality Constraint for Electrcardiographic Inverse Solution", Journal of Electrocardiology, vol. 35, No. 4, Oct. 1, 2002, pp. 55-73.

Geneser, et al: "The Influence of Stochastic Organ Conductivity in 20 ECG Forward Modeling: A Stockhastic Finite element Study", Engineering in Medicine and Biology Society, 2005. IEEE-EMBS 2005. 27th Annual International Conference of the Shanghai, China Sep. 1-4, 2005, Piscataway, NJ,VUSA, IEEE, Jan. 1, 2005, pp. 5528-5531.

Applicant: Cardiolnsight Technologies, Inc.; International Search Report and Written Opinion; International Application No. PCT/US2019/014107; Filed: Jan. 18, 2019; 13 pgs.

\* cited by examiner

DETERMINING BIPOLAR ELECTRICAL ACTIVITY

TECHNICAL FIELD

This disclosure relates to systems, computer readable media and methods for determining bipolar electrical activity.

BACKGROUND

Electroanatomical mapping is a broad term that covers several modes of mapping for a body surface, such as the heart or brain. Some examples of cardiac mapping are endocardial mapping and epicardial mapping. The mapping can be utilized to generate an image, such as an isochronal image, for displaying electrophysiological information. One type of cardiac map is an activation map, which can be used to display activation time patterns on a surface of the heart.

SUMMARY

As one example, one or more computer-readable media have computer-executable instructions for performing a method. The method includes storing geometry data representing a primary geometry of a cardiac envelope that includes nodes distributed across the cardiac envelope and geometry of a body surface that includes locations where electrical signals are measured. The body surface is spaced apart from the cardiac envelope. The method also includes perturbing the primary geometry of the cardiac envelope a given distance and direction to define the perturbed geometry of the cardiac envelope including nodes spaced from the nodes of the primary geometry. The method also includes computing reconstructed bipolar electrical signals on the nodes of the primary cardiac envelope based on the electrical signals measured from the body surface and the geometry data, including the primary and perturbed geometries of the cardiac envelope.

As another example, a system includes memory and a processor. The memory is to store instructions and data. The data includes electrical data representing electrical signals measured on a body surface for at least one time interval. The data also includes geometry data representing a primary geometry of a cardiac envelope, including nodes distributed across the cardiac envelope, and geometry of a body surface including measurement locations for the electrical signals measured on the body surface. The processor is to access the memory and execute the instructions. The instructions are to at least compute reconstructed bipolar electrical signals on to nodes residing on the primary cardiac envelope based on the electrical data and the geometry data, including the primary geometry and a perturbed geometry of the cardiac envelope.

DETAILED DESCRIPTION

This disclosure relates to computer readable media, systems and methods to construct bipolar electrical activity for a geometric surface, such as corresponding to a cardiac surface (e.g., epicardial and/or endocardial surface). The geometric surface onto which the bipolar electrical activity is reconstructed is spaced apart from locations where electrical signals are measured. For example, electrical signals can be measured by body surface electrodes distributed across an outer surface of a patient's body and a geometric surface can correspond to a surface within the patient's body spaced radially inwardly from the measurement locations. The approach disclosed herein provides a solution to the inverse problem that enables bipolar electrical information to be recovered directly from the body surface measurements. For example, the solution provides a linear mathematical relationship between the function of the body surface boundary condition and bipolar electrical signals on the geometric surface.

Figure 1:
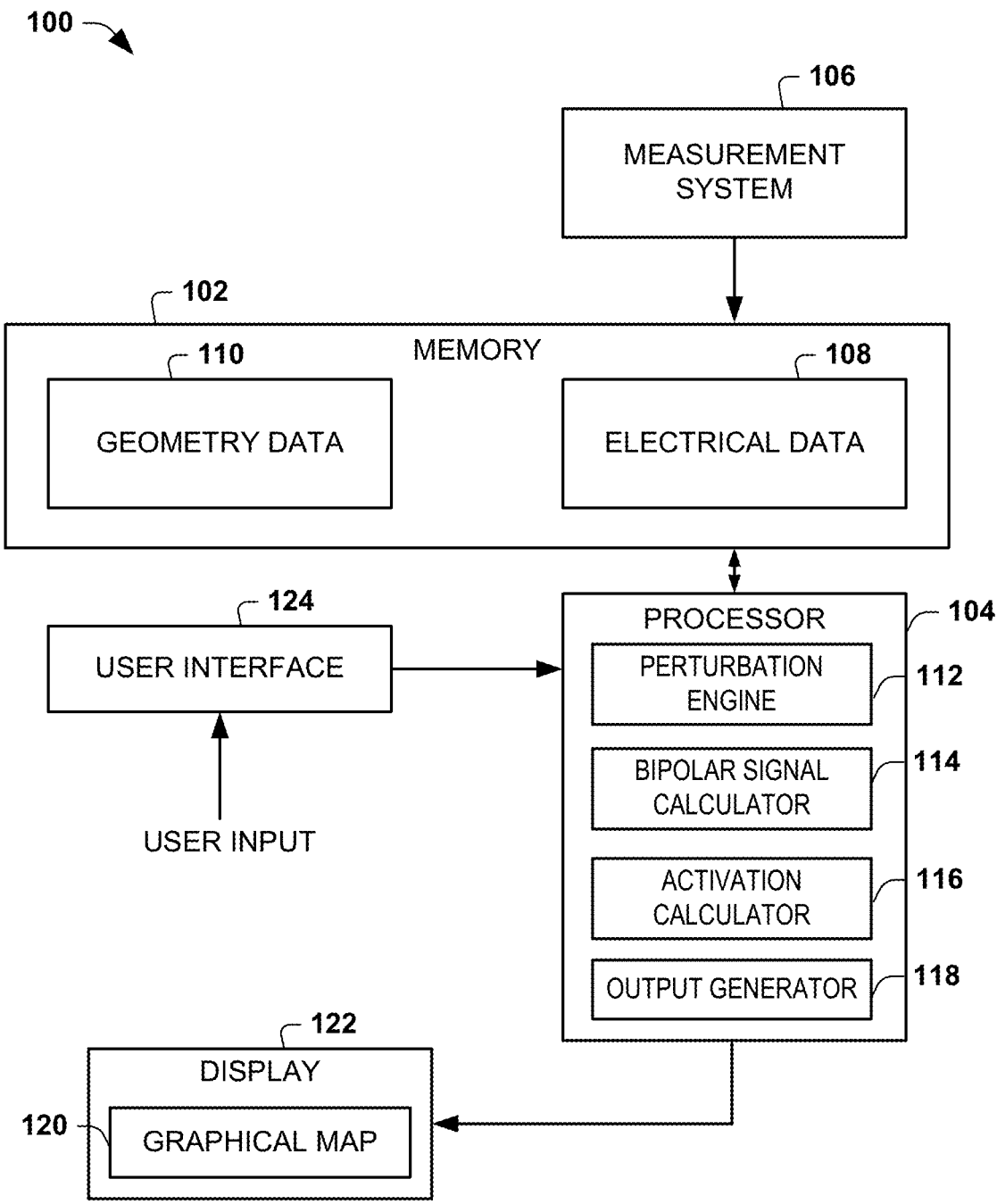
FIG. 1 depicts an example of a system to determine and display bipolar electrical activity.

FIG. 1 depicts an example of a system 100 that can be utilized to reconstruct bipolar electrical signals on a cardiac envelope. As used herein, a cardiac envelope may refer to any two-dimensional or three-dimensional surface residing inside the patient's body on to which electrical signals are to be reconstructed. For example, the surface can be a virtual surface (e.g., a sphere) or a surface of an anatomical structure (e.g., an epicardial or endocardial surface). For example, the cardiac envelope can be represented as a mesh structure in three-dimensional space that is registered in or can be registered into a patient's anatomy. The mesh structure may include nodes distributed across a geometry representing the cardiac envelope.

In the example of FIG. 1, the system 100 is demonstrated as a computing apparatus that includes memory 102 and a processor 104. The memory can store data and instructions that can be accessed by the processor 104 to perform the methods and functions disclosed herein. Also demonstrated in FIG. 1 is a measurement system 106 that can measure electrical signals from the body surface and store the measured electrical signals as electrical data 108 in the memory 102. The electrical data 108 may include real time measurements of electrical signals and/or previous measurements. For example, the measurement system 106 includes a plurality of electrodes distributed across a patient's torso (e.g., thorax region) to provide the electrical signals according to electrical signals provided at the locations where the signals are measured over one or more time intervals. Examples of a non-invasive sensor array that can be used as electrodes in the measurement system 106 are shown and described in U.S. Pat. No. 9,655,561, which was filed Dec. 22, 2011, or in International patent application No. PCT/US2009/

063803, which was filed Nov. 10, 2009, each of which applications is incorporated herein by reference.

The memory 102 also stores geometry data 110. The geometry data 110 can represent locations where the electrical signals are measured by the measurement system 106. The geometry data can also include information representing a geometry of a cardiac envelope. The cardiac envelope may be a geometrical construct, such as a sphere or other three-dimensional shape approximating the size of the heart or be smaller or larger than the heart. As another example, the geometry may be a three-dimensional mesh structure configured to represent the epicardial surface of a heart, such as generic heart or the heart of the patient where the electrical signals are measured. The body surface locations where the electrical signals are measured by measurement system 106 are spaced apart from (e.g., circumscribing) the cardiac envelope. The geometry data 110 and the electrical data 108 can be combined to provide electroanatomical data (representing measured electrical activity and spatial position where measurements are made).

The geometry data 110 can be generated from image data that is acquired using nearly any imaging modality. Examples of imaging modalities include ultrasound, computed tomography (CT), 3D Rotational angiography (3DRA), magnetic resonance imaging (MRI), x-ray, positron emission tomography (PET), and the like. Such imaging can be performed separately (e.g., before or after the measurements) utilized to generate the electrical data 108. Alternatively, imaging may be performed concurrently with recording the electrical activity that is utilized to generate the electrical data 108.

The processor 104 is configured to compute reconstructed bipolar electrical signals on the cardiac envelope based on the electrical data 108 and the geometry data 110. By way of example, the processor 104 includes a perturbation engine 112 to perturb the geometry data 110 associated with the cardiac envelope. Thus, the geometry data 110 for the cardiac envelope includes data representing a primary geometry for the cardiac envelope and a perturbed geometry that represents perturbed locations of nodes distributed across the cardiac envelope. The primary geometry is the surface onto which the electrical activity is reconstructed. The perturbed geometry corresponds to spatial variations for node locations in the primary geometry, such as disclosed herein. The perturbation engine 112 may be programmed to perturb the locations of the nodes distributed across the cardiac envelope for a set of perturbations to provide the perturbed geometry data. For example, each of the perturbations displace nodes on the cardiac envelope according to a perturbation vector, such that each node is moved a known distance and direction from its initial node location on the cardiac envelope. The perturbed geometry data may be determined and stored in memory prior to computing the reconstructed bipolar electrical signals or perturbed geometry may be computed as part of such computations. The perturbation engine 112 can provide a number of one or more perturbations, such as representing a set of perturbation vectors for each of the nodes on the cardiac envelope.

A bipolar signal calculator 114 computes reconstructed bipolar electrical signals on the cardiac envelope based on the electrical signals at the measurement locations and the geometry data 110, including both the initial and perturbed node locations for the cardiac envelope. The bipolar signal calculator 114 may compute reconstructed bipolar electrical signals on the cardiac envelope for each perturbation of the geometry data and for each of a plurality of time samples over which the electrical data 108 has been obtained by the measurement system 106.

As an example, the bipolar signal calculator 114 computes the reconstructed bipolar electrical signals based on a difference between the potential of a given node at the initial location on the cardiac envelope and the potential of a the given node at each perturbed location in the set of perturbations. The resulting bipolar electrical signals for each of the nodes thus correspond to a bipolar vector having a magnitude and direction. The magnitude of the bipolar vectors corresponds to the calculated difference between the potentials at the initial location and a selected perturbed location. The direction of the bipolar vector for each of the node correspond to a direction along a virtual line extending from the initial node location to the perturbed node location for which the resulting bipolar electrical signal is computed. As mentioned, the bipolar electrical signals are computed for the measured electrical signals over one or more time intervals which results in a set of bipolar signal vectors for each respective time sample and for each node on the cardiac envelope.

The bipolar signal calculator 114 selects one of the bipolar vectors for each node on the cardiac envelope for each time sample. For example, the bipolar signal calculator 114 compares the magnitude of the bipolar vectors computed for the set of perturbation at a given node and respective time sample to identify a strongest bipolar signal for each respective node and time sample. Thus, the number of perturbations will determine the accuracy of the resulting bipolar signal for each node. For example, each node on the cardiac envelope will provide a bipolar vector having a magnitude and direction, and the bipolar signal calculator 114 selects bipolar vector for each node having the largest magnitude to specify the strongest bipolar signal. The bipolar signal calculator 114 repeats the comparison for each of the time samples in the one or more time intervals and thereby identifies a bipolar vector for each of the nodes for each of the time samples and the resulting reconstructed electrograms are stored in memory to define bipolar electrical activity across the cardiac envelope. The repeating of the comparison for the different nodes and time instances does not require an iterative process, as the comparisons may be performed concurrently (e.g., in parallel) by respective instances of the bipolar signal calculator 114.

As a further example, the bipolar signal calculator 114 computes the reconstructed electrical signals according to a bipolar forward model that is derived to express electrical activity on the body surface as a function of a body transformation matrix, such as disclosed herein. The bipolar signal calculator 114 further solves the inverse computation of the bipolar forward model to estimate the bipolar electrical activity on the cardiac envelope based on the measured body surface electrical activity provided by the electrical data for the one or more time intervals. As mentioned, the bipolar signal calculator 114 determines the bipolar electrical activity on the cardiac envelope for each perturbation to provide a corresponding set of reconstructed bipolar signal vectors for each node on the cardiac envelope. For example, the bipolar signal calculator 114 is further programmed to solve the inverse computation by regularizing the transformation matrix to estimate an inverse of the bipolar transformation matrix. The bipolar electrical signals on the cardiac envelope are calculated based on the inverse bipolar transformation matrix, which is estimated by such regularization, and the measured body surface electrical activity stored in the memory 102.

The processor 104 may also include an activation calculator 116 that is programmed to compute activation information for the bipolar electrical signals that have been computed by signal calculator 114 and stored in the memory 102. The activation calculator may compute an activation time. Additionally or alternatively, the activation calculator 116 can compute activation time and direction based on the bipolar signal vectors that have been computed by the bipolar signal calculator 114. The bipolar time and activation thus can be represented as an activation vector, corresponding to the time (vector magnitude) and direction of activation for nodes across the cardiac envelope for each beat cycle in the one or more time intervals represented by the electrical data 108.

The processor 104 can include an output generator 118 that is programmed to generate a graphical map or other outputs 120 that can be provided to a display device 122. For example, the graphical map 120 may include a two- or three-dimensional visualization of the bipolar electrical signals computed across the cardiac envelope over one or more time intervals. Additionally or alternatively, the graphical map 120 may include a graphical representation of the activation time or activation time and direction (activation vector) across the envelope for each beat cycle in the one or more time intervals for which the measurements have been made.

The type of output and the time interval over which the bipolar electrical signals are reconstructed can be set in response to a user input provided to the processor 104 via a user interface 124. For example, the user interface 124 may include a graphical user interface (GUI) programmed to enable a user to select one or more time intervals as well as to control the appearance (e.g., viewing angle) of the visualization provided in the graphical map 120. For example, a user can rotate the 2-D or 3-D graphical map of the cardiac envelope as well as determine the type of information that is presented on the map based on the reconstructed bipolar electrical signals that are computed by the processor 104. The resulting graphical map and presentation of bipolar electrical signals in the output 120 enables an enhanced characterization of activation patterns and that are approximate actual bipolar electrograms. Moreover, by perturbing the geometry as part of the reconstruction of electrical signals that are being reconstructed, activation direction for each of the nodes across the cardiac envelope are provided along with the activation time for each bipolar electrical signal.

Figure 2:
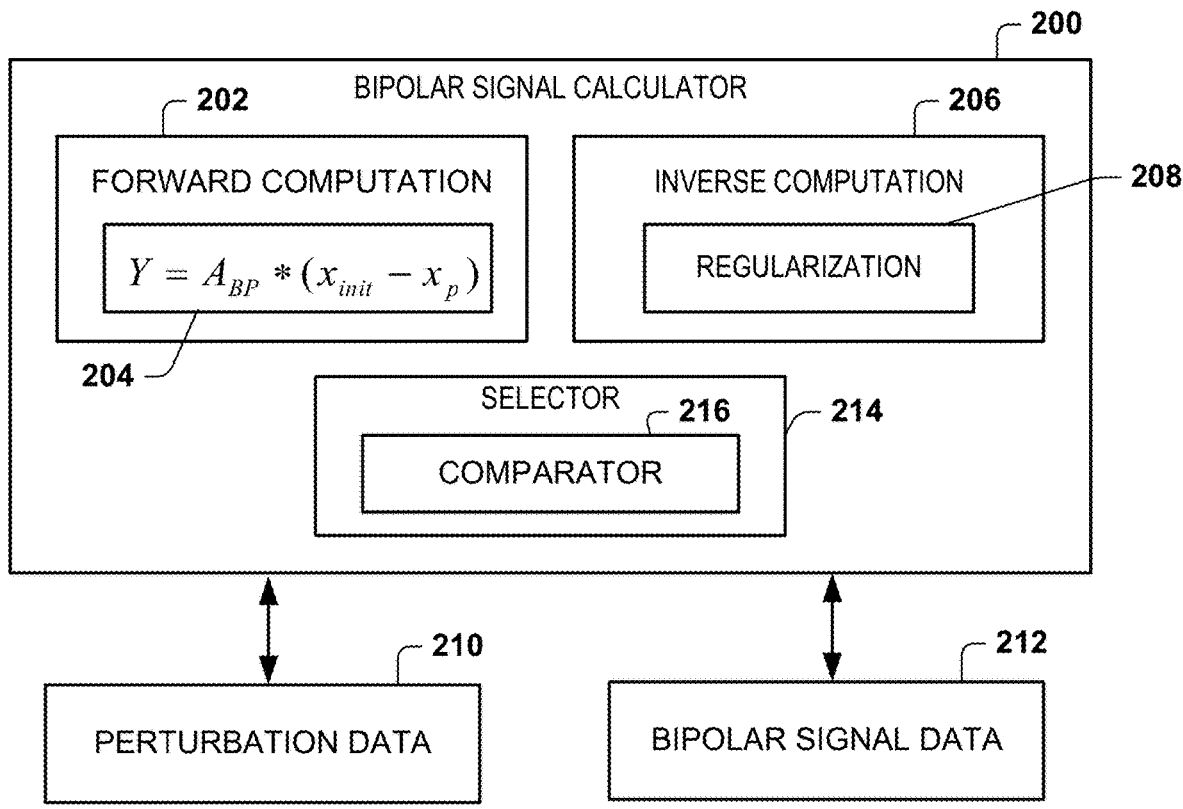
FIG. 2 depicts an example of a bipolar signal calculator.

FIG. 2 depicts an example of a bipolar signal calculator 200. The bipolar signal calculator 200 includes a forward computation 202 programmed to derive a forward model 204 to express electrical activity on the body surface (e.g., where the measurement system 106 measures electrical signals on the body surface) as a function of a bipolar transformation matrix ($A_{BP}$) and the bipolar electrical activity on the cardiac envelope. By way of example, the electrical activity on the body surface (Y) may be represented as a function of a transformation matrix ($A_1$) and the potential on the cardiac envelope ($X_1$) for the original initial geometry of the cardiac envelope may be expressed as follows:

$$Y = A_1 * X_1 \qquad (1)$$

and taking the inverse of (1), may be expressed as follows:

$$INV(A_1)Y = INV(A_1)A1 * X_1 \approx X_1 \qquad (2)$$

Similarly, the electrical activity on the body surface (y) may be represented as a function of a transformation matrix ($A_2$) and the potential on the cardiac envelope for a given perturbation at a displaced location ($X_2$) may be expressed as follows:

$$Y = A_2 * X_2 \qquad (3)$$

and taking the inverse of (3), results in the following:

$$INV(A_2)Y = INV(A_2)A_2 * X_2 \approx X_2. \qquad (4)$$

By combining the (2) and (4), an estimation of the bipolar electrical activity may be provided in a combined forward model, as follows:

$$(INV(A_1) - INV(A_2))Y = X_1 - X_2 \qquad (5)$$

Let $$Y_{new} = INV(INV(A_1) - INV(A_2)) * (INV(A_1) - INV(A_2))Y$$

and $$A_{new} = INV(INV(A_1) - INV(A_2))$$

such that $$Y_{new} = A_{new} * \Delta X \qquad (6)$$

The result is a corresponding forward model 204, as demonstrated in (6), which can be utilized to solve the inverse problem and determine the bipolar electrical activity across the cardiac envelope. For example, the bipolar signal calculator 200 also includes an inverse computation 206 that uses the forward model 204 to estimate bipolar electrical activity for nodes on the cardiac envelope based on measured body surface electrical activity (Y) for each time sample of a given time interval. The inverse computation 206 further can include regularization that is applied to estimate the inverse of the bipolar transformation matrix ($A_{BP}$) 208, such that the inverse computation 206 can determine the bipolar electrical activity ($X_1 - X_2$) based on the inverse of the transformation matrix and the measured body surface electrical activity (Y).

As mentioned, the bipolar signal calculator 200 determines the bipolar electrical signals across the cardiac envelope for each of a plurality of perturbations. There can be any number of perturbations, each of which may be displaced a distance and direction from an initial node location. For example, each node can be perturbed according to plurality of perturbation vectors, such as to define plurality of perturbation node locations displaced relative to each initial node location.

Figure 3:
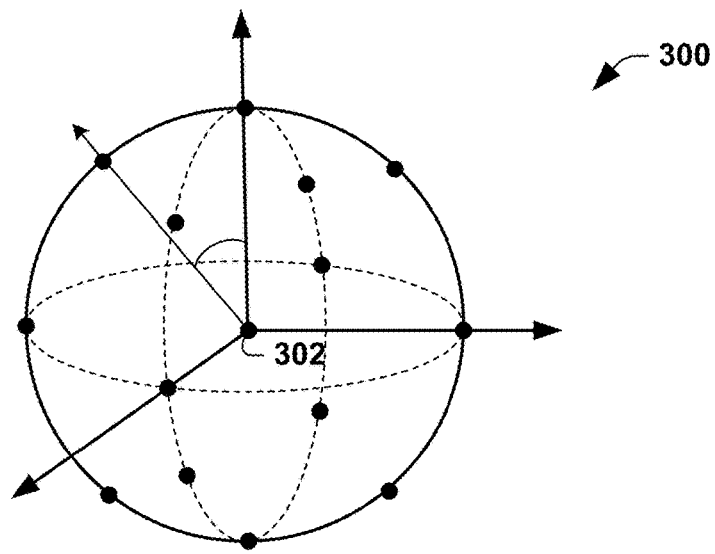
FIG. 3 depicts an example of a three-dimensional perturbation space that can be used for displacing nodes to steer bipolar electrical activity.

For example, in FIG. 3, a sphere 300 is shown that includes an initial location 302 at a center of the sphere and a plurality of perturbation locations 304 distributed on the surface of the sphere, where each perturbation location is spaced an equal distance from the initial center location 302. Each perturbation location thus may be represented in three-dimensional space in Cartesian or polar coordinates as a spatial vector having a distance and direction from an initial location. For each perturbation vector that is applied to each node on the cardiac envelope, a set of bipolar electrical signals (e.g., electrograms) are computed for each respective node on the cardiac envelope. The perturbation locations (e.g., perturbation vectors) can be stored in perturbation data 210 such as in memory 102 of FIG. 1. The perturbation data thus provides displacement distance and direction for each of the perturbations that are implemented as part of the computation for the bipolar electrical signals by the bipolar signal calculator 200.

As shown in the example of FIG. 3, the set of perturbations can be uniformly distributed in three-dimensional space, such that each node on the cardiac envelope resides near a center of the set of perturbations that are applied for each respective node. In other examples, the perturbation locations may be selected in a desired pattern or randomly in space. The number and placement of perturbations thus can determine the accuracy or resolution of the steering function that ultimately results in the strongest bipolar electrical activity for each of the plurality of nodes.

Referring back to FIG. 2, for each perturbation, the bipolar signal calculator 200 employs the inverse computation 206 with respect to the forward model 204 to compute the bipolar electrical activity at each node on the cardiac envelope. The corresponding bipolar electrical data for each of the perturbations can be stored in memory as bipolar signal data 212.

Since bipolar electrical activity is computed for each perturbation, the bipolar signal calculator 200 also includes a selector 214 to identify which bipolar signal to utilize at a given node for each time sample. For example, the selector 214 includes a comparator 216 that compares the magnitude of bipolar vectors computed for the set of perturbations at a given a node and given time sample to identify a strongest bipolar signal for such given node and given time sample. Thus the comparator 216 can identify the strongest bipolar signals and its direction across the cardiac envelope for time samples in one or more time intervals for which electrical measurements have been acquired (e.g., on the surface of the patient's torso). By utilizing multiple perturbations and identifying the strongest bipolar signal for each node, steerability is implemented and captured in the resulting bipolar electrical signals that are identified for each node on the cardiac envelope.

The selector 214 is configured to repeat the comparison for each of the time samples and the time interval (or intervals) to identify the strongest bipolar electrical signal for each of the nodes in each of the time samples. The strongest identified bipolar signals for each node and each time sample are stored in memory to provide corresponding reconstructed bipolar electrical signals for the time interval which can be stored in memory as the bipolar signal data 212.

Figure 4:
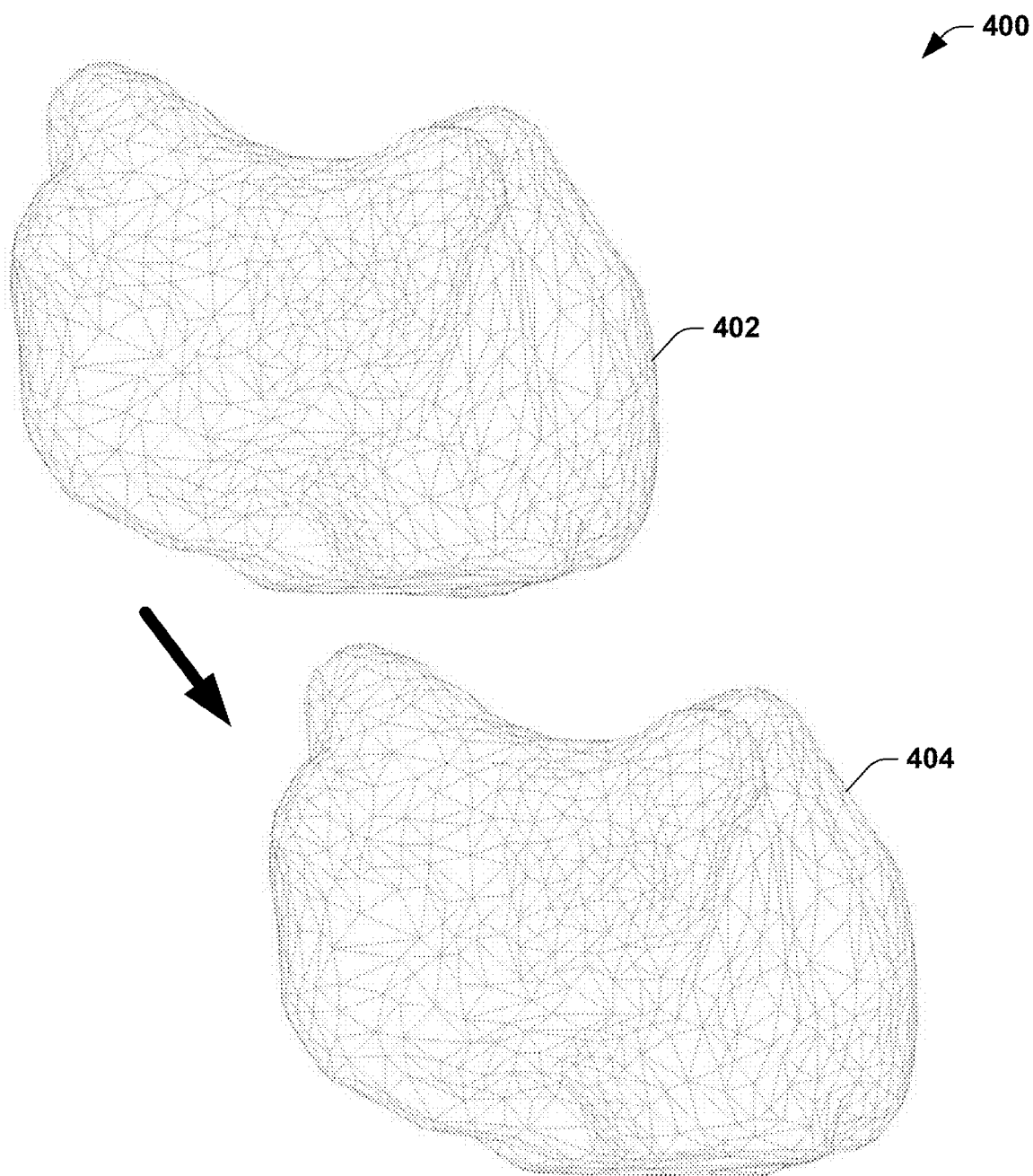
FIG. 4 depicts an example of an initial and a perturbed surface geometry that can be utilized for computing bipolar electrical activity.

FIG. 4 depicts an example of cardiac envelopes 400 showing an initial cardiac envelope 402 and a perturbed cardiac envelope 404 that is displaced a given direction and orientation relative to the initial location (e.g., according to a perturbation vector, such as shown in FIG. 3). The number and location of the perturbations of the cardiac envelope can vary according to application requirements. In the example of FIG. 4, the cardiac envelope 402 is demonstrated as a triangular mesh surface corresponding to an epicardial surface of a heart. Vertices (e.g., nodes) of the mesh correspond to locations on the cardiac envelope for which electrical activity is being reconstructed. Thus, the locations in 402 correspond to an initial cardiac envelope and the locations in 404 correspond to perturbed locations that have been displaced according to application of a perturbation vector to the initial locations. Accordingly, a calculated difference between the electrical signal for each of the locations on the first envelope 402 and respective (perturbed) locations on the second envelope 404 provides a bipolar signal value for each of the respective locations on the cardiac envelope. As disclosed herein, bipolar signals can similarly be computed over a plurality of perturbation vectors and over one or more time intervals, each containing plurality of time samples.

Figure 5:
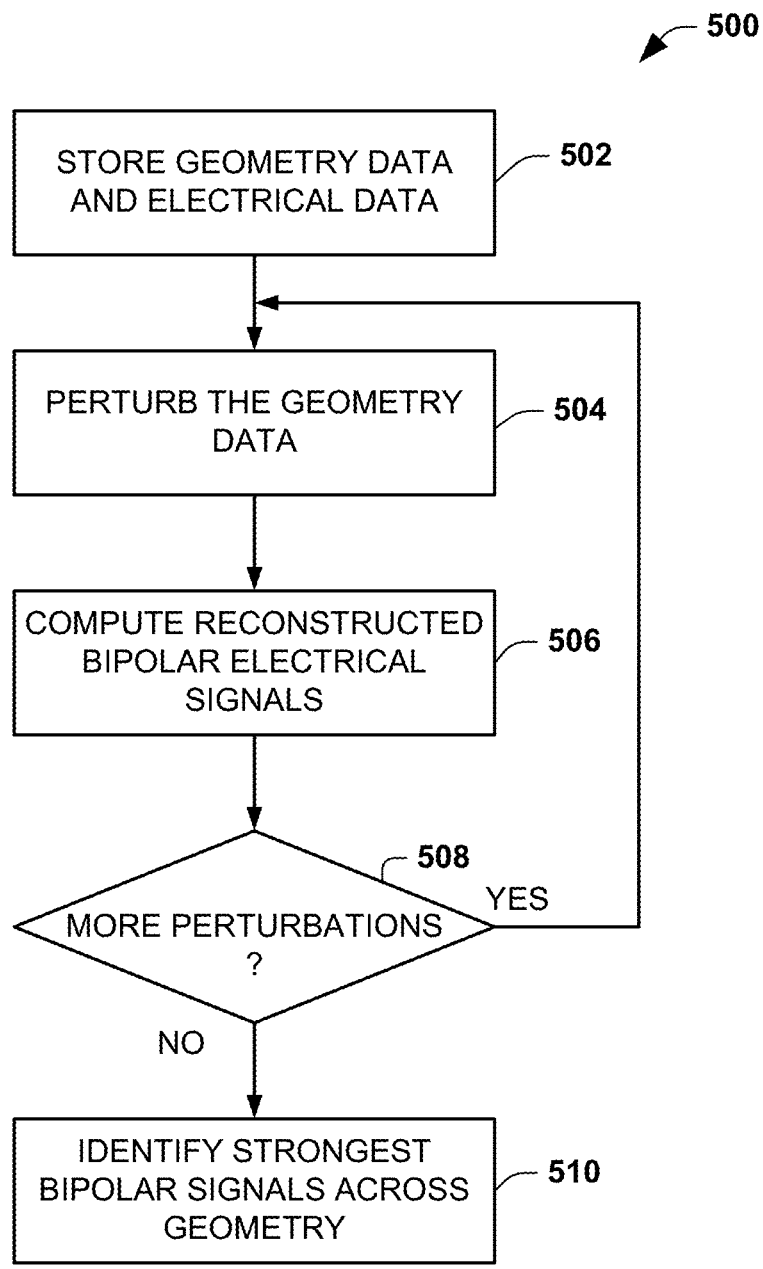
FIG. 5 is a flow diagram depicting an example of a method to determine bipolar electrical activity.
Figure 6:
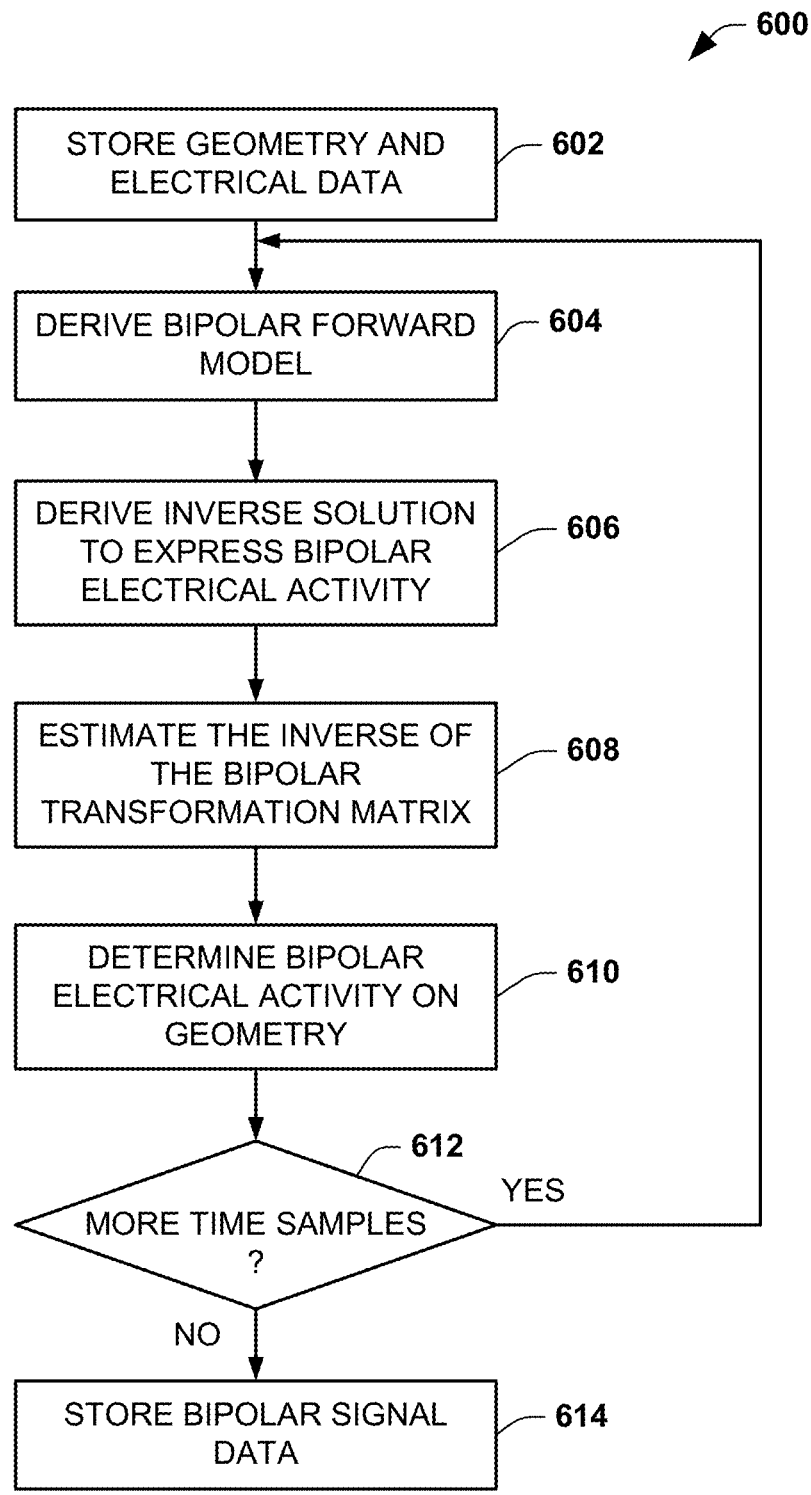
FIG. 6 is a flow diagram depicting another example of a method to reconstruct bipolar electrical activity on an envelope.

In view of the foregoing structural and functional features described above, methods in accordance with various aspects of the present disclosure will be better appreciated with reference to FIGS. 5 and 6. While, for purposes of simplicity of explanation, the method of FIGS. 5 and 6 are shown and described as executing serially, it is to be understood and appreciated that the present disclosure is not limited by the illustrated orders, as some aspects could, in other examples, occur in different orders and/or concurrently from that shown and described herein. Moreover, not all illustrated features may be required to implement the methods.

FIG. 5 depicts an example to determine bipolar electro activity. The method 500 begins at 502 in which geometry data is stored. Electrical data can also be stored at 502, which may include electrical data that was previously measured from the body surface or is being measured intraprocedurally (e.g., in real time). For example, the data may be stored in memory storage device, such as random access memory (RAM, such as static RAM or dynamic RAM), a solid state drive, hard disk drive storage, which may be internal or external to the computer implementing the method 500.

At 504, the geometry is perturbed. The geometry may include a cardiac envelope onto which the electrical activity (e.g., electrophysiological signals, such as electrograms) is being reconstructed. For example, the cardiac envelope onto which the electrical activity is being reconstructed can be perturbed according to a perturbation vector. Thus, at 504, each of a plurality of nodes on the cardiac envelope may be displaced from an original location on the cardiac envelope to its perturbed location by a given distance at a given direction defined by the perturbation vector.

At 506, reconstructed bipolar electrical signals are computed. As disclosed herein, the bipolar electrical signals can be reconstructed onto the cardiac envelope based on the geometry data and the measured body surface electrical activity. For example, the reconstructed bipolar electrical signals can be determined on the by solving the inverse problem as a function of a difference between the reconstructed electrical signal value for each original location on the cardiac envelope and the electrical signal value at each respective perturbed location on the cardiac envelope.

At 508, a determination is made as to whether more perturbations are to be implemented. If more perturbations exist, the method returns from 508 to 504 in which the geometry is perturbed again. The perturbation can be from the initial location or the perturbation can be perturbed according to a vector from the previously perturbed location until the set of perturbations, which may be predetermined or determined based on the values of bipolar electrical signals as computed at 506, have been completed at 508. From 508 after no additional perturbations are to be performed the method proceeds to 510.

At 510 the strongest bipolar signals across the geometry are identified. For example, the bipolar signals determined at a given time instance for each node on the cardiac envelope for the set of perturbations are evaluated and compared. The strongest bipolar electrical signal computed for each node on the envelope at the given time instance (from those computed from the set of perturbations) can be tagged to define the bipolar signals for the cardiac envelope for the given time instance. The identified bipolar signals can be aggregated for each time instance stored in memory. The corresponding bipolar electrical signals can be aggregated over a series of time instances (to provide reconstructed bipolar electrical signals across the cardiac envelope over one or more time intervals such as disclosed herein.

FIG. 6 is a flow diagram depicting an example method for computing bipolar electrical signals. The method 600 begins at 602 in which geometry and electrical data is stored. As disclosed herein, the geometry data may represent geometry of electrodes distributed across the body surface of a patient as well as geometry of patient anatomy (i.e., actual geometry or a model). The electrical data may correspond to electrical data that is being measured in real time and/or data that has previously acquired. At 604, a bipolar forward model is derived. For example, the forward model represents the electrical signals on the body surface as a function of a transformation matrix and bipolar potentials distributed on a cardiac envelope, such as disclosed herein (see, e.g., Equation 5 or 6).

At 606, an inverse solution is derived to express bipolar electrical activity. For example, the inverse solution is utilized for reconstructing bipolar electrical signals on the cardiac envelope as disclosed herein. The cardiac envelope can correspond to an actual surface of the heart, or any cardiac envelope that resides within the body beneath the body surface on which the electrical activity is measured. The inverse problem is ill-posed. Accordingly, at 608 the inverse of the bipolar transformation matrix is estimated. The estimation may be performed by various regularization techniques, such as Tikhonov regularization or calculating a method of fundamental solution. Examples of these regularization techniques that may be implemented at 608 are disclosed in the above-incorporated U.S. Pat. Nos. 6,772,004 and 7,983,743. In other examples, other regularization methods may be utilized, such as Lasso, elastic net and total variation methods. For example, the inverse computation may be applied directly to Eq. 5.

At 610, bipolar electrical activity is determined on the geometry of interest, such as the cardiac envelope. The bipolar electrical activity for each of the nodes may be determined according to the approach described with respect to FIG. 5, such as where computations of bipolar electrical signals for each node over a set of perturbations is used to steer the method to identify a strongest bipolar electrical signal for each node.

At 612, a determination is made as to whether there are additional time samples of the electrical data. If more time samples exist, the method returns from 612 to 604 to determine the bipolar electrical activity for the next time sample. The derivations at 604 and 606 may utilize the same system of equations, but include the new values of electrical signals on the body surface for the next time sample for estimating bipolar electrical activity. If it is determined that no more samples exist at 612, the method can proceed to 614 to store the bipolar signal data in suitable memory.

Figure 7:
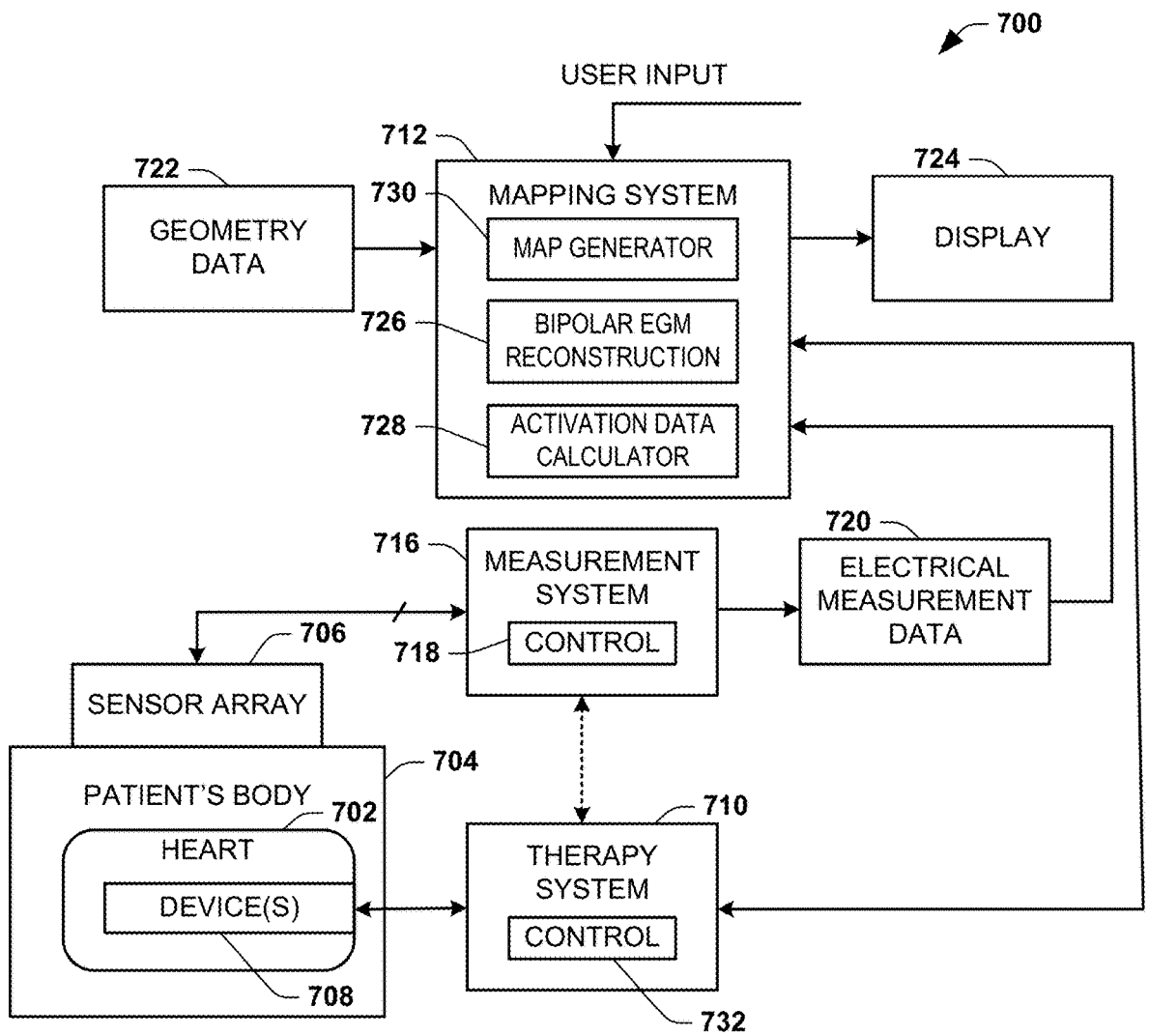
FIG. 7 depicts an example of a system to measure and display bipolar electrical information in conjunction with an evasive procedure.

FIG. 7 depicts an example of a system 700 that can be utilized for performing diagnostics and/or treatment of a patient 704. In some examples, the system 700 can assess of the heart 702 in real time (intraprocedurally) as part of a diagnostic and/or treatment procedure, such as to help a physician deliver a therapy to the patient 704 (e.g., delivery location, amount and type of therapy).

In the example of FIG. 7, a sensor array 706 includes one or more electrodes that can be utilized for recording patient activity. As one example, the sensor array 706 can correspond to a high-density arrangement of body surface sensors (e.g., greater than 200 electrodes) that are distributed over a portion of the patient's thorax for measuring electrical activity associated with the patient's heart (e.g., as part of an electrocardiographic mapping procedure). Examples of a non-invasive sensor array that can be used as the sensor array are shown and described in the above-incorporated U.S. Pat. No. 9,655,561 and in International patent application No. PCT/US2009/063803. Other arrangements and configurations of sensing electrodes can be used as the sensor array 706 in other examples. The array 706 can be a reduced set of electrodes, which that does not cover the patient's entire torso and is designed for measuring electrical activity for a particular purpose (e.g., an array of electrodes specially designed for analyzing AF and/or VF).

In some examples, one or more sensors may also be located on a device 708 that is configured for insertion into the patient's body via a low or minimally invasive procedure (e.g., an electrophysiology (EP) study). In some examples, the device 708 can be utilized in conjunction with the sensor array 706 for mapping (e.g., by mapping system 712) electrical activity for an endocardial surface such as the wall of a heart chamber. Additionally or alternatively, the device 708 can be localized within the heart 702, which can be registered into an image or map that is generated by the system 700.

The sensor array 706 includes electrodes coupled (e.g., via electrically conductive wires or traces) to provide the sensed electrical information (e.g., electrical potential measurements) to a corresponding measurement system 716. The measurement system 716 can include appropriate controls and signal processing circuitry 718 for providing corresponding measurement data 720 that describes electrical activity measured by the sensors in the sensor array 714. The measurement data 720 can include analog or digital information.

The control 718 can also be configured to control the data acquisition process (e.g., sampling rate) for measuring electrical activity and providing the measurement data 720 over time. The measurement data 720 can be acquired concurrently in the absence of or in conjunction with the delivering therapy by the therapy system, such as to detect electrical activity of the heart 702 that occurs in response to applying a given therapy (e.g., according to therapy parameters).

The mapping system 712 is programmed to combine the measurement data 720, corresponding to body surface electrical activity (e.g., electrical potential measurements) from the heart 702, with geometry data 722 by applying appropriate processing and computations (e.g., as disclosed with respect to FIGS. 1-6) to generate a corresponding output. For instance, the mapping system 712 can generate output data including a graphical representation of bipolar electrical activity across the cardiac envelope (e.g., on a surface of the heart 702). The output data can be supplied to a graphics pipeline and provided to a display 724 via a display interface (not shown).

The mapping system 712 includes signal processing methods programmed to, when executed by one or more processors, transform the geometry data 722 and measurement data 720 into actionable health information. In the example of FIG. 7, the signal processing methods include a bipolar electrogram reconstruction method 726, an activation data calculator 728 and a map generator 730. For example, the bipolar electrogram reconstruction method 726 is programmed to compute reconstructed bipolar electrical signals on a cardiac envelope based on the electrical measurement data 720 and the geometry data 722. As disclosed herein, the bipolar reconstruction method may perturb geometry of the cardiac envelope for a set of perturbations (according to a perturbation vector) at each of a plurality of time samples. The bipolar electrogram reconstruction method 726 thus may solve the inverse problem to estimate the bipolar electrograms for the nodes on the cardiac envelope (e.g., as defined by the geometry data) for each perturbation for each of the plurality of time samples. The magnitude of bipolar electrograms computed for each of the perturbations at a given node and time sample are compared with respect to each other to identify a strongest bipolar signal for such given node and time sample. The comparison is thus repeated for each of the time samples to identify the strongest bipolar signal for each of the nodes on the cardiac envelope (e.g., the heart surface) at each of the time samples.

The activation data calculator 728 further can compute activation time for the nodes on the cardiac envelope from the reconstructed bipolar electrical signals. The activation data calculator 728 may compute an activation time. Additionally or alternatively, the activation calculator 116 can compute activation time and direction based on bipolar signal vectors that have been computed by the bipolar signal calculator. That is, since each bipolar signal is derived from a pair of locations (a node on the cardiac envelope and a perturbed location), the resulting bipolar signal can be provided as a vector having both magnitude and direction.

The map generator 730 is programmed to generate a graphical map based on the reconstructed bipolar electrical signals, which may be a static map or dynamic map that varies as a function of time (e.g., stepping through time instances of one or more time intervals. The map generator 730 may also generate the graphical map to display one or both of activation time and direction of activation corresponding to the reconstructed bipolar electrical signals computed over a time interval. Since the measurement system 716 can, in some examples, measure electrical activity for the entire heart concurrently, the resulting output data (e.g., bipolar electrograms or derivations thereof) thus can also represent concurrent data for the heart in a temporally and spatially consistent manner. The time interval for which the output data/maps are computed can be selected based on user input. Additionally or alternatively, the selected intervals can be synchronized with the application of therapy by the therapy system 708.

As disclosed herein, the geometry data 722 may represent three-dimensional geometry of the patient's torso (where the sensor array 706 is positioned) and the cardiac envelope to where the bipolar electrograms are being reconstructed. For example, the geometry data 722 may be derived from and/or including image data acquired for the patient. Such image processing can include extraction and segmentation of anatomical features, including one or more organs and other structures, from a digital image set. Additionally, a location for each of the electrodes in the sensor array 706 can be included in the geometry data 722, such as by acquiring the image while the electrodes are disposed on the patient and identifying the electrode locations in a coordinate system through appropriate extraction and segmentation. The resulting segmented image data can be converted into a two-dimensional or three-dimensional graphical representation that includes the region of interest for the patient.

By way of further example, the geometry data 722 can be acquired using nearly any imaging modality (e.g., x-ray, ultrasound, computed tomography, magnetic resonance imaging, or the like) based on which a corresponding representation can be constructed, such as described herein. Such imaging may be performed concurrently with recording the electrical activity that is utilized to generate the patient electrical measurement data 720 or the imaging can be performed separately (e.g., before the measurement data has been acquired).

Alternatively, the geometry data 722 can correspond to a mathematical model, such as can be a generic model or a model that has been constructed based on image data for the patient. Appropriate anatomical or other landmarks, including locations for the electrodes in the sensor array 714 can be identified in the geometry data 722 to facilitate registration of the electrical measurement data 720 and computing the inverse solution for reconstructing bipolar electrograms thereon. The identification of such landmarks can be done manually (e.g., by a person via image editing software) or automatically (e.g., via image processing techniques).

As a further example, a catheter, such as a pacing catheter or ablation catheter, having one or more therapy delivery devices 708 affixed thereto can be inserted into the body 704 as to contact the patient's heart 702 at one or more locations, endocardially or epicardially. Those skilled in the art will understand and appreciate various type and configurations of therapy delivery devices 708 that can be utilized, which can vary depending on the type of treatment and the procedure.

For example, the therapy device 708 can include one or more electrodes located at a tip of an ablation catheter configured to generate heat for ablating tissue in response to electrical signals (e.g., radiofrequency energy) supplied by a therapy system 710. In other examples, the therapy delivery device 708 can be configured to deliver cooling to perform ablation (e.g., cryogenic ablation), to deliver chemicals (e.g., drugs), ultrasound ablation, high-frequency ablation, or a combination of these or other ablation mechanisms. In still other examples, the therapy delivery device 708 can include one or more electrodes located at a tip of a pacing catheter to deliver electrical stimulation, such as for pacing the heart, in response to electrical signals (e.g., pacing pulses) supplied by a therapy system 710. Other types of therapy can also be delivered via the therapy system 708 and the invasive therapy delivery device 708 that is positioned within the body 704.

The therapy system 710 can be located external to the patient's body 704 and be configured to control therapy that is being delivered by the device 708. For instance, the therapy system 710 includes control circuitry 732 that can communicate (e.g., supply) electrical signals via a conductive link electrically connected between the device (e.g., electrodes) 708 and the therapy system 710. The control system 732 can control parameters of the signals supplied to the device 708 (e.g., current, voltage, repetition rate, trigger delay, sensing trigger amplitude) for delivering therapy (e.g., ablation or stimulation) via the device(s) 7084 to one or more location of the heart 702.

The control circuitry 732 can set the therapy parameters and apply stimulation based on automatic, manual (e.g., user input) or a combination of automatic and manual (e.g., semiautomatic controls). One or more sensors (not shown) can also communicate sensor information back to the therapy system 708. In some examples, the mapping system 712 communicates with the therapy system 710 through a physical or wireless link. In this way the mapping system 712 may supply control information (e.g., commands), such as derived from reconstructed bipolar electrical signals, to the therapy system 710. The therapy system 710 thus can interpret the control information to control delivery of the therapy to the heart 702 via the device 708. Additionally or alternatively, such as where the device 708 includes one or more sensors (e.g., sensing electrodes), the therapy system 710 can communicate electrical measurement data for cardiac electrical activity measured directly from the heart.

Figure 8:
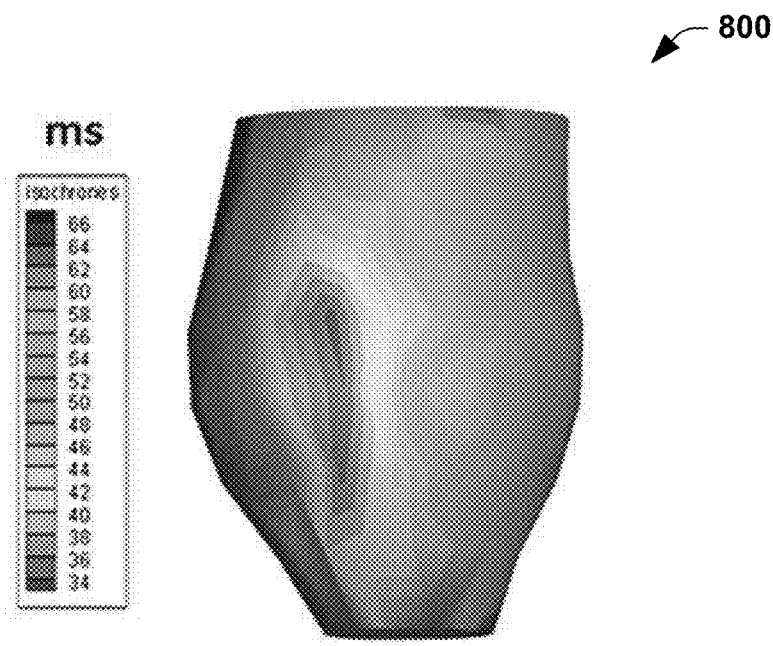
FIG. 8 depicts an example of a graphical map to display bipolar electrical information.
Figure 9:
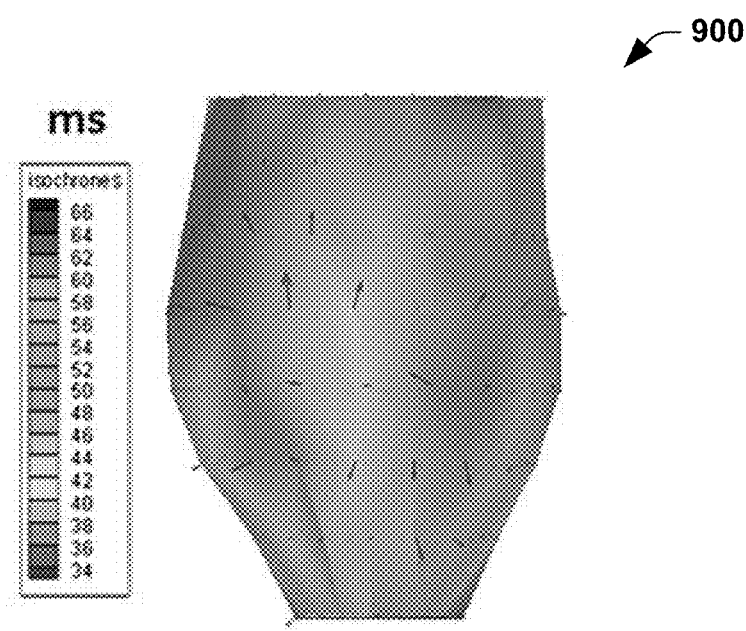
FIG. 9 depicts another example of a graphical map displaying bipolar electrical activity and direction across a geometric surface.

FIGS. 8 and 9 depict examples of epicardial graphical maps 800 and 900 that may be generated (e.g., by output generator 118 or map generator 730) to visualize reconstructed bipolar electrograms. FIG. 8 depicts an example of a graphical map 800 to display activation time across a tank-torso model based on reconstructed bipolar electrical signals generated according to this disclosure. The graphical map in FIG. 9 depicts both activation time and activation direction derived from reconstructed bipolar electrical signal (which include bipolar vectors having both magnitude and direction). The example maps of bipolar electrical activity shown in FIGS. 8 and 9 afford greater accuracy compared to similar approaches that may generate maps based on unipolar electrical signals. For instance, bipolar epicardial electrograms reconstructed, as disclosed herein, have higher correlation coefficient (e.g., measuring the morphology accuracy) and smaller relative error (e.g., measuring magnitude accuracy) compared to the many existing unipolar reconstructed epicardial electrograms.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on one or more computer-usable storage media having computer readable program code on such media. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. One or more computer-readable media having computer-executable instructions for performing a method comprising:
   storing geometry data representing a primary geometry of a cardiac envelope that includes nodes distributed across the cardiac envelope and geometry of a body surface that includes locations where electrical signals are measured, the body surface being spaced apart from the cardiac envelope;
   perturbing the primary geometry of the cardiac envelope, including respective nodes thereof, a given distance and direction to define a perturbed geometry of the cardiac envelope including nodes spaced from the respective nodes of the primary geometry; and
   computing reconstructed bipolar electrical signals on the nodes of the primary cardiac envelope based on the electrical signals measured from the body surface and the geometry data, the geometry data including the primary and perturbed geometries of the cardiac envelope.

2. The media of claim 1, wherein the method further comprise storing electrical data representing the measured electrical signals on the body surface over at least one time interval, the reconstructed bipolar electrical signals being computed on the cardiac envelope for each of a plurality of time samples during the time interval.

3. The media of claim 2, wherein the nodes of the cardiac envelope are perturbed for a set of perturbations at each of the plurality of time samples, each perturbation in the set of perturbations displacing the nodes of the cardiac envelope a known distance and direction from the respective nodes of the primary geometry, the reconstructed bipolar electrical signals are computed for each perturbation in the set of perturbations for each of the plurality of time samples.

4. The media of claim 3, wherein computing reconstructed bipolar electrical signals includes calculating a difference between an electrical potential of a given node of the primary geometry of the cardiac envelope and an electrical potential of the given node at each perturbed node location of the cardiac envelope.

5. The media of claim 4, wherein each of the reconstructed bipolar electrical signals for each of nodes on the cardiac envelope is computed as a bipolar vector having a magnitude and direction, the magnitude corresponding to the calculated difference and the direction corresponding to a direction along a virtual line extending from a node location of the primary geometry to the corresponding perturbed node location in the corresponding perturbed geometry.

6. The media of claim 5, wherein the method further comprises:
   comparing the magnitude of the bipolar vectors computed for the set of perturbations at the given node and time sample to identify a strongest bipolar signal for the given node and time sample; and
   repeating the comparison for each of the time samples in the time interval to identify the strongest bipolar signal for each of the nodes in each of the time samples, the strongest bipolar signal for each of the nodes in each of the time samples being stored in memory as the reconstructed bipolar electrical signals on the primary geometry of the cardiac envelope for the time interval.

7. The media of claim 3, wherein the set of perturbations are uniformly distributed in three-dimensional perturbation space such that each respective node of the primary geometry of the cardiac envelope resides near a center of the perturbation space for the respective node.

8. The media of claim 1, wherein computing the reconstructed bipolar electrical signals further comprises:
deriving a bipolar forward model expressing the electrical signals on the body surface as a function of a bipolar transformation matrix and the reconstructed bipolar electrical signals on the primary geometry of the cardiac envelope; and
solving an inverse computation of the bipolar forward model to determine the reconstructed bipolar electrical signals on the primary geometry of the cardiac envelope based on the electrical signals measured from the body surface.

9. The media of claim 8, wherein solving the inverse computation further comprises regularizing the bipolar transformation matrix to estimate an inverse of the bipolar transformation matrix, the reconstructed bipolar electrical signals on the cardiac envelope being determined based on the inverse of the bipolar transformation matrix and the electrical signals measured from the body surface.

10. The media of claim 8, wherein the nodes of the cardiac envelope are perturbed for a set of perturbations at each of a plurality of time samples, each perturbation displacing the primary geometry of the cardiac envelope a respective distance and direction to define the perturbed geometry of the cardiac envelope, such that the nodes of the perturbed geometry are spaced from the nodes of the primary geometry,
wherein the reconstructed bipolar electrical signals are computed for each perturbation in the set of perturbations for each of the plurality of time samples as a bipolar vector, having a magnitude and direction, based on a difference between an electrical potential of each respective node of the primary geometry and an electrical potential of its corresponding node of the perturbed geometry.

11. The media of claim 10, wherein for each node of the primary geometry of the cardiac envelope, the method further comprising:
comparing a magnitude of the bipolar vector computed for each respective node over the set of perturbations to identify a strongest bipolar signal for each respective node; and
storing the strongest bipolar signal for each of the nodes as the reconstructed bipolar electrical signal for the respective node.

12. The media of claim 1, wherein the method further comprises:
generating a graphical map that displays at least one of the activation time and direction of activation corresponding to the reconstructed bipolar electrical signals computed over a time interval.

13. The media of claim 1, wherein the measured electrical signals comprise unipolar electrograms measured non-invasively using a plurality of body surface electrodes distributed on a portion patient's torso.

14. One or more computer-readable media having computer-executable instructions for performing a method comprising:
storing geometry data representing a primary geometry of a cardiac envelope that includes nodes distributed across the cardiac envelope and geometry of a body surface that includes locations where electrical signals are measured, the body surface being spaced apart from the cardiac envelope;
perturbing the primary geometry of the cardiac envelope a given distance and direction to define a perturbed geometry of the cardiac envelope including nodes spaced from the nodes of the primary geometry;
computing reconstructed bipolar electrical signals on the nodes of the primary cardiac envelope based on the electrical signals measured from the body surface and the geometry data, including the primary and perturbed geometries of the cardiac envelope;
comparing the magnitude of bipolar vectors computed for the set of perturbations at a given node of the primary geometry and a given time sample to identify a strongest bipolar signal for the given node and time sample; and
repeating the comparison for each of a series of time samples in a time interval to identify respective strongest bipolar signals for each of the nodes of the primary geometry in each of the time samples in the time interval, the strongest bipolar signal for each of the nodes in each of the time samples being stored in memory as the reconstructed bipolar electrical signals on the primary geometry of the cardiac envelope for the time interval.

15. The media of claim 14, wherein the nodes of the cardiac envelope are perturbed for a set of perturbations at each of a plurality of time samples, and wherein the set of perturbations are uniformly distributed in three-dimensional perturbation space such that each respective node of the primary geometry of the cardiac envelope resides near a center of the perturbation space for the respective node.

16. The media of claim 14, wherein computing the reconstructed bipolar electrical signals further comprises:
deriving a bipolar forward model expressing the electrical signals on the body surface as a function of a bipolar transformation matrix and the reconstructed bipolar electrical signals on the primary geometry of the cardiac envelope; and
solving an inverse computation of the bipolar forward model to determine the reconstructed bipolar electrical signals on the primary geometry of the cardiac envelope based on the electrical signals measured from the body surface.

17. The media of claim 16, wherein solving the inverse computation further comprises regularizing the bipolar transformation matrix to estimate an inverse of the bipolar transformation matrix, the reconstructed bipolar electrical signals on the cardiac envelope being determined based on the inverse of the bipolar transformation matrix and the electrical signals measured from the body surface.

18. The media of claim 16, wherein the nodes of the cardiac envelope are perturbed for a set of perturbations at each of a plurality of time samples, each perturbation displacing the primary geometry of the cardiac envelope a respective distance and direction to define the perturbed geometry of the cardiac envelope, such that the nodes of the perturbed geometry are spaced from the nodes of the primary geometry,
wherein the reconstructed bipolar electrical signals are computed for each perturbation in the set of perturbations for each of the plurality of time samples as a bipolar vector, having a magnitude and direction, based on a difference between an electrical potential of each respective node of the primary geometry and an electrical potential of its corresponding node of the perturbed geometry.

19. The media of claim 18, wherein for each node of the primary geometry of the cardiac envelope, the method further comprises:
comparing a magnitude of the bipolar vector computed for each respective node over the set of perturbations to identify a strongest bipolar signal for each respective node; and
storing the strongest bipolar signal for each of the nodes as the reconstructed bipolar electrical signal for the respective node.

20. The media of claim 14, wherein the method further comprises generating and displaying via a graphical user interface a graphical map that displays at least one of the activation time and direction of activation corresponding to the reconstructed bipolar electrical signals computed over a time interval.

21. One or more computer-readable media having computer-executable instructions for performing a method comprising:
storing geometry data representing a primary geometry of a cardiac envelope that includes nodes distributed across the cardiac envelope and geometry of a body surface that includes locations where electrical signals are measured, the body surface being spaced apart from the cardiac envelope;
perturbing the primary geometry of the cardiac envelope a given distance and direction to define a perturbed geometry of the cardiac envelope including nodes spaced from the nodes of the primary geometry; and
computing reconstructed bipolar electrical signals on the nodes of the primary cardiac envelope based on the electrical signals measured from the body surface and the geometry data, including the primary and perturbed geometries of the cardiac envelope,
wherein the nodes of the cardiac envelope are perturbed for a set of perturbations at each of a plurality of time samples, and wherein the set of perturbations are uniformly distributed in three-dimensional perturbation space such that each respective node of the primary geometry of the cardiac envelope resides near a center of the perturbation space for the respective node.

22. The media of claim 21, wherein computing the reconstructed bipolar electrical signals further comprises:
deriving a bipolar forward model expressing the electrical signals on the body surface as a function of a bipolar transformation matrix and the reconstructed bipolar electrical signals on the primary geometry of the cardiac envelope; and
solving an inverse computation of the bipolar forward model to determine the reconstructed bipolar electrical signals on the primary geometry of the cardiac envelope based on the electrical signals measured from the body surface.

23. The media of claim 22, wherein solving the inverse computation further comprises regularizing the bipolar transformation matrix to estimate an inverse of the bipolar transformation matrix, the reconstructed bipolar electrical signals on the cardiac envelope being determined based on the inverse of the bipolar transformation matrix and the electrical signals measured from the body surface.

24. The media of claim 22, wherein the nodes of the cardiac envelope are perturbed for a set of perturbations at each of a plurality of time samples, each perturbation displacing the primary geometry of the cardiac envelope a respective distance and direction to define the perturbed geometry of the cardiac envelope, such that the nodes of the perturbed geometry are spaced from the nodes of the primary geometry,
wherein the reconstructed bipolar electrical signals are computed for each perturbation in the set of perturbations for each of the plurality of time samples as a bipolar vector, having a magnitude and direction, based on a difference between an electrical potential of each respective node of the primary geometry and an electrical potential of its corresponding node of the perturbed geometry.

25. The media of claim 24, wherein for each node of the primary geometry of the cardiac envelope, the method further comprises:
comparing a magnitude of the bipolar vector computed for each respective node over the set of perturbations to identify a strongest bipolar signal for each respective node; and
storing the strongest bipolar signal for each of the nodes as the reconstructed bipolar electrical signal for the respective node.

26. The media of claim 21, wherein the method further comprises generating and displaying via a graphical user interface a graphical map that displays at least one of the activation time and direction of activation corresponding to the reconstructed bipolar electrical signals computed over a time interval.

* * * * *